United States Patent [19]

Ritter

[11] Patent Number: 5,411,041
[45] Date of Patent: May 2, 1995

[54] APPARATUS FOR REMOVING DEBRIS FROM BETWEEN AND AROUND TEETH

[76] Inventor: Charles H. Ritter, P.O. Box 12126, Tallahassee, Fla. 32317

[21] Appl. No.: 156,765

[22] Filed: Nov. 24, 1993

[51] Int. Cl.6 ............................................. A61C 15/00
[52] U.S. Cl. .................................... 132/322; 132/323
[58] Field of Search ............... 132/322, 323, 324, 325, 132/326, 327, 309

[56] References Cited

U.S. PATENT DOCUMENTS

| | | | |
|---|---|---|---|
| 924,543 | 6/1909 | Dysart | 132/324 |
| 1,217,264 | 2/1914 | Baxter | 132/327 |
| 1,475,986 | 12/1922 | Cooke . | |
| 1,488,214 | 3/1924 | Mason | 132/309 |
| 2,187,899 | 1/1940 | Henne | 132/323 |
| 3,378,017 | 10/1965 | Stiles . | |
| 3,421,524 | 9/1966 | Waters . | |
| 3,472,247 | 4/1967 | Borsum et al. . | |
| 3,534,745 | 10/1970 | Waters . | |
| 3,746,017 | 7/1973 | Casselman | 132/325 |
| 3,759,274 | 9/1973 | Warner . | |
| 3,847,167 | 11/1974 | Brien . | |
| 3,927,686 | 12/1975 | Zambito . | |
| 4,014,354 | 3/1977 | Garrett . | |
| 4,235,253 | 11/1980 | Moore | 132/322 |
| 4,245,658 | 1/1981 | Lecouturier . | |
| 4,265,257 | 5/1981 | Salyer . | |
| 4,307,740 | 12/1981 | Florindez et al. . | |
| 4,333,197 | 6/1982 | Kuris | 433/119 |
| 4,338,957 | 7/1982 | Meibauer . | |
| 4,458,702 | 7/1984 | Grollimund | 433/29 |
| 4,698,869 | 10/1987 | Mierau et al. | 15/105 |
| 4,706,695 | 11/1987 | Urso . | |
| 4,727,894 | 3/1988 | Meibauer . | |
| 4,736,757 | 4/1988 | Badoux . | |
| 4,830,032 | 5/1989 | Jousson | 132/323 |
| 5,016,660 | 5/1991 | Boggs | 132/322 |
| 5,020,179 | 6/1991 | Scherer | 15/22.1 |
| 5,069,233 | 12/1991 | Ritter | 132/322 |
| 5,170,809 | 12/1992 | Imai et al. | 132/323 |

*Primary Examiner*—Cary E. O'Connor
*Attorney, Agent, or Firm*—Shlesinger Arkwright & Garvey

[57] ABSTRACT

An apparatus for removing debris from between and around teeth including a main body member having first and second ends and a flossing implement operably associated therewith. The flossing implement is detachably connected to the main body member. The flossing implement includes first and second ends. The first end of the flossing implement is disposed adjacent the first end of the main body member. The second end of the flossing implement is removed from the first end of the main body member. The second end of the flossing implement includes first and second tines and an intermediate section connecting the first and second tines. The first and second tines each include projections for receiving the corresponding ends of the flossing material extending therebetween. Alternatively, or in addition, the first and second tines may be formed hollow and the intermediate section provided with an opening for receiving a removable flossing cartridge. Preferably, a protective housing is provided to house the flossing implement. A drive motor is operably connected to the flossing implement for reciprocally displacing the same.

19 Claims, 2 Drawing Sheets

U.S. Patent May 2, 1995 Sheet 1 of 2 5,411,041
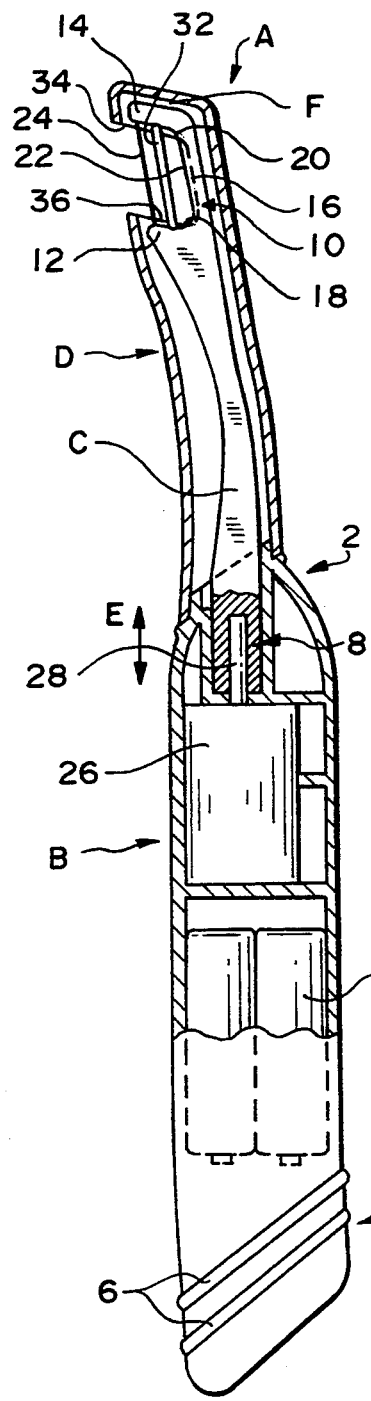
FIG. 1
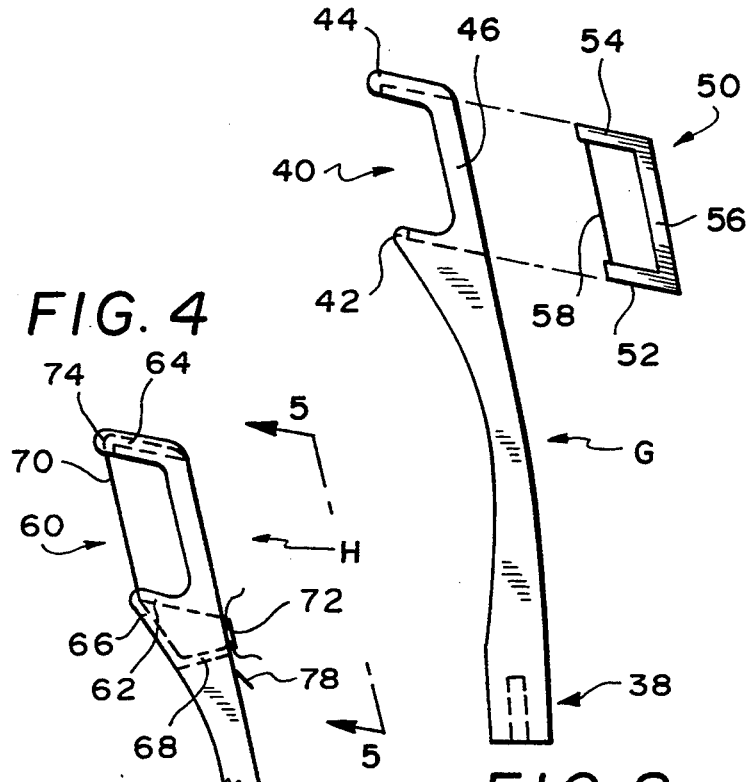
FIG. 4
FIG. 2
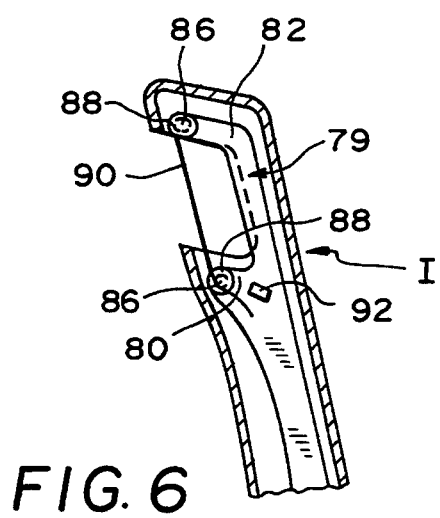
FIG. 6

APPARATUS FOR REMOVING DEBRIS FROM BETWEEN AND AROUND TEETH

FIELD OF THE INVENTION

The present invention is directed generally to implements for aiding individuals in practicing proper dental hygiene. More specifically, a preferred embodiment of the present invention is directed to a dental flosser for removing debris located around and lodged between an individual's teeth.

BACKGROUND OF THE INVENTION

The importance of practicing proper dental hygiene has been well documented. In this regard, it is extremely advantageous to frequently and systematically remove plaque and debris from around and between an individual's teeth. Failure to religiously remove debris and plaque from between and around teeth is likely to lead to dental disease including tooth decay, gingivitis and the like.

Countless configurations of toothbrushes have been proposed to remove plaque. However, it is widely accepted by dentists, periodontists and dental hygienists that it is not possible to reach a number of remote areas of dental sulcuses by using a toothbrush alone. Dental floss or tape has been used to remove plaque from these hard to reach areas. Customarily, an individual manipulates the dental floss with both hands to remove debris from remote areas of dental sulcuses. This manner of removing debris has numerous disadvantages. Specifically, this manner of flossing is time consuming and extremely tedious. Moreover, it requires a level of dexterity beyond that of many individuals. For example, it is extremely difficult and/or painful for handicapped persons and those suffering from arthritis and similar ailments to floss their teeth in this manner.

Several implements have been proposed to overcome the disadvantages associated with the aforementioned manual method of flossing teeth. The following U.S. patents are directed to implements of this nature: U.S. Pat. Nos. 3,421,524; 3,472,247; 3,534,745; 3,759,274; 3,847,167; 4,014,3545; 4,235,253; 4,245,658; 4,265,257; 4,338,957; 4,458,702; 4,605,2025; 4,706,695; 4,727,894; and 4,8930,032. The dental flossers described in these U.S. patents have several inherent disadvantages. Generally speaking, previously known dental flossers are extremely complex. As a result, these devices are laborious and expensive to manufacture. Moreover, their complex construction makes servicing such devices difficult. Further, some previously known automatic flossers include at least one exposed reciprocating element which upon coming into contact with sensitive oral tissues will likely cause an individual discomfort.

A significant number of prior dental flossers are designed such that the flossing material traverses an arcuate path. An individual using such a device must exercise caution, since movement of these types of flossers in either a vertical or horizontal direction may result in the flossing material rubbing sensitive oral tissues. Therefore, an individual is likely to restrict movement of such devices. Because such devices cannot be readily moved in a vertical or horizontal direction, it is extremely more likely that hard to reach areas will be missed.

Some previously known flossers have included a flossing material which moves linearly. Flossers of this type commonly employ complex feeding systems for the floss or alternatively require a specialized flossing material which must be replaced after every use.

Further, the design of some previously known flossers makes it difficult to dispose of and replace dental floss after each use.

Finally, it is noted that some conventional dental flossers do not include any means for restricting the proximity of the dental floss material with respect to the surrounding oral tissues. Therefore, if conventional flossers are improperly used, offensive touching of the flossing material against the oral tissues may occur.

OBJECTS AND SUMMARY OF THE INVENTION

It is an object of the present invention to provide a new and improved apparatus for removing debris from between and around teeth.

Another object of the present invention is to provide an automatic dental flosser wherein all moving elements are encased in a protective housing to avoid possible injury or discomfort to the consumer.

A further object of the present invention is to provide a dental flosser which is designed such that a user may readily and easily replace used flossing material.

Yet a further object of the present invention is to provide a dental flosser having a flossing implement. The flossing implement includes a pair of tines optimally oriented to readily accommodate the natural orientation of an individual's lower and upper teeth.

Still a further object of the present invention is to provide a dental flosser with a cutting element for cutting flossing material to the desired size.

Yet still another object of the present invention is to provide a dental flosser which may be readily operated by the handicapped and/or other persons suffering from ailments such as arthritis and the like.

A further object of the present invention is to provide a dental implement which may be readily converted from a flosser to a toothbrush.

Still a further object of the present invention is to provide a dental flosser with a stop means for regulating the proximity of the flossing material to sensitive oral tissues thereby minimizing the likelihood of contact between the flossing material and the oral tissues.

In summary, the preferred embodiment of the present invention is directed to an apparatus for removing debris from between and around teeth including a main body member having first and second ends and a flossing implement operably associated therewith. Preferably, the flossing implement is detachably connected to the main body member. The flossing implement includes first and second ends. The first end of the flossing implement is disposed adjacent the first end of the main body member. The second end of the flossing implement is removed from the first end of the main body member. The second end of the flossing implement includes first and second tines and an intermediate section connecting the first and second tines. The flossing implement includes at least one projection for receiving the ends of the flossing material extending between the first and second tines. Alternatively, or in addition, the first and second tines may be formed hollow and the intermediate section provided with an opening for receiving a removable flossing cartridge. Preferably, a protective housing is provided to house the flossing implement. A drive motor is operably connected to the flossing implement for reciprocally displacing the same relative to the protective housing.

The above objects, advantages and summary of the present invention are in no way intended to limit the scope of the claims. Moreover, the above identified objects and advantages are not an exhaustive compilation. Rather, other advantages will be readily apparent upon review of the following detailed description of the preferred embodiment.

DETAILED DESCRIPTION OF THE DRAWINGS

FIG. 1 is a side elevational view of a dental flosser formed in accordance with the preferred embodiment of the present invention having a portion thereof broken away.

FIG. 2 is an exploded side elevational view of an alternative form of a flossing implement.

FIG. 4 is a fragmentary side elevational view of another alternative form of flossing implement.

FIG. 6 is a fragmentary side elevational view of a further alternative form of the present invention.

Figure 5:
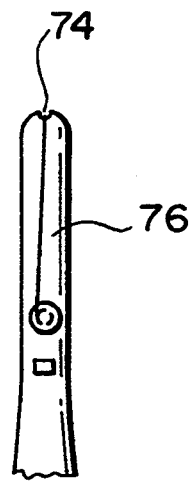
FIG. 5 is a plan view of the alternative form illustrated in FIG. 4.

DETAILED DESCRIPTION OF THE PREFERRED AND ALTERNATIVE EMBODIMENTS OF THE PRESENT INVENTION

The preferred and several alternative forms of the present invention will now be described with reference made to the accompanying drawings.

FIG. 1

Referring to FIG. 1, an automatic dental flosser A includes a body B and a flossing element C. A protective cover D houses the flossing element C. The protective cover D is detachably connected to body B. Preferably, the connection between body B and cover D is a snug or press fit to permit ease of detachment. However, any conventional means may be provided for detachably connecting the cover D to body B.

Body B includes first end 2 and second end 4. A pair of outwardly projecting ribs 6 are disposed adjacent the second end 4 of body B. Ribs 6 assist the individual in gripping the dental flosser A. The flossing element C is provided with a slight arcuate configuration to assist the individual in reaching remote areas of dental sulcuses. The flossing element C includes a first end 8 and a second end 10. The first end 8 is positioned adjacent the first end 2 of body B. The second end 10 is positioned removed from first end 2 of body B.

The second end 10 of flossing element C includes a pair of tines 12 and 14. As readily seen from FIG. 1, first tine 12 is positioned closer to first end 2 of body B than tine 14. Preferably, tines 12 and 14 are aligned with each other relative to the longitudinal axis of flossing implement C. An intermediate section 16 connects tines 12 and 14.

Tines 12 and 14 each have inner surfaces 18 and 20, respectively. Inner surface 18 extends substantially parallel to inner surface 20. Inner surface 20 of tine 14 forms an obtuse angle with inner surface 22 of intermediate section 16. Inner surface 18 of tine 12 forms an acute angle with inner surface 22 of intermediate section 16. This angular relationship between tines 12 and 14 and intermediate section 16 is important to accommodate for the natural orientation of an individual's upper and lower teeth.

A flossing material 24 extends between the tines 12 and 14. As illustrated in FIG. 1, the ends of flossing material 24 are permanently embedded in the corresponding tines 12 and 14. In this embodiment, the entire flossing element C is designed to be disposed after each use. Further, the protective cover D may also be designed to be disposed after each use. By providing a disposable flossing implement C and protective housing D, the dental flosser A may be used by a number of persons without the likelihood of disease being transmitted.

The body B houses drive motor 26 having an output shaft 28. Preferably, the drive motor reciprocally displaces output shaft 28 along a straight line path designated by arrows E. As seen in FIG. 1, the first end 8 of flossing implement C is detachably mounted on output shaft 28. Therefore, the reciprocal motion of output shaft 28 is in turn transmitted to flossing implement C. It will be readily appreciated that the upward displacement of output shaft 28 does not exceed the distance F between tine 14 and the corresponding inner surface of protective housing D. The reciprocal straight line motion of output shaft 28 may be achieved in any conventional manner. For example, an eccentric drive system may be employed similar to that disclosed in my previously issued U.S. Pat. No. 5,069,233 the entire disclosure of which is herein incorporated by reference.

Figure 3:
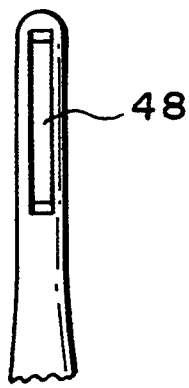
FIG. 3 is a fragmentary plan view of the alternative form illustrated in FIG. 2 with the flossing cartridge omitted.

More specifically, an eccentric drive arrangement similar to that illustrated in FIGS. 2 through 4 and described in the corresponding passages of my earlier patent identified above may be used. In this instance, output shaft 28 would be provided with two spaced projections extending substantially perpendicular to the longitudinal axis of body member B. An eccentric would be disposed intermediate the spaced projections and mounted on a rotary drive shaft extending from a conventional drive. The rotary drive shaft would be oriented substantially perpendicular to the path of travel E of output shaft 28.

It will be readily appreciated that numerous other arrangements may be provided for imparting the desired reciprocal straight line path of output shaft 28. Preferably, the motor 26 is powered by batteries 30. Alternatively, an alternating current potential with a plug and cord arrangement or other conventional power source may be used. Also an ultrasound motor can be used.

A stop 32 extends between upper and lower portions 34 (See FIG. 1) and 36, respectively, of protective housing D. The stop 32 limits the movement of dental floss 24 relative to an individual's sensitive oral tissues thereby reducing the likelihood of injury. The functions of stop 32 will not be further elaborated upon since they are disclosed in my earlier issued U.S. Pat. No. 5,069,233 the entire disclosure of which has been incorporated herein by reference. It should be noted that stop 32 may be adjustable as described in this patent.

FIGS. 2 AND 3

Referring to FIGS. 2 and 3, an alternative form of the present invention will now be described. The dental flosser in this embodiment is identical to that disclosed in FIG. 1 with the sole exception being a modification to the flossing implement G.

The flossing implement G includes first and second ends 38 and 40, respectively. First end 38 is identical to first end 8 of flossing implement C. As seen in FIG. 2, second end 40 includes first and second tines 42 and 44 respectively and an intermediate section 46. The orientation of tines 42 and 44 and intermediate section 46 is the same as the corresponding elements illustrated in FIG. 1. Referring to FIG. 3, an opening 48 is provided in the exterior surface of flossing element G and communicates with the hollow cavities formed in tines 42 and 44. A removable flossing cartridge or support member 50 is similarly shaped to tines 42 and 44 and intermediate section 46 so that cartridge 50 may be received therein. Preferably, the cartridge 50 is slightly oversized to snugly lodge in the second end 40 of flossing element G. However, it will be readily appreciated that numerous other arrangements may be employed for removably securing the cartridge 50 in the second end 40 of flossing element G.

As is readily seen in FIG. 2, the cartridge 50 includes a paired of spaced legs 52 and 54 and a connecting section 56. A flossing material 58 extends between the spaced legs 52 and 54. It will be readily appreciated that the cartridge 50 is disposed of after each use.

FIGS. 4 AND 5

Referring to FIGS. 4 and 5, another alternative form will now be described. This form is identical to the dental flosser illustrated in FIG. 1 with the sole exception of the second end 60 of flossing element H. The second end 60 includes a pair of tines 62 and 64. The tine 62 includes a groove 66 which communicates with a hole 68 extending through the width of flossing implement H. The groove 66 and hole 68 receive a portion of the flossing material 70 and permit an individual to wrap the corresponding end around projection 72. A groove 74 is formed in tins 64. The groove 74 receives a portion of the flossing material 70. The flossing material 70 continues along the top surface 76 of second end 60 and the corresponding end is wrapped around projection 72 as seen in FIG. 5. This arrangement allows an individual to readily replace the flossing material without discarding any portion of the flossing implement.

A cutting element 78 is provided on the top surface 76 in order that an individual may readily cut the dental floss to the desired size. It will be noted that the cutting element 78 is not exposed to the individual since it is housed in a protective cover similar to that illustrated in FIG. 1.

FIG. 6

Referring to FIG. 6, a further alternative embodiment will now be described. As is readily appreciated, the stop has been omitted. The stop is an optional feature in all embodiments and may be included if desired.

The second end 79 of flossing element I is very similar to that illustrated in FIG. 1. Tines 80 and 82 each additionally include an outwardly projecting member 86. The outwardly projecting members 86 each include an annular recess 88 so that the corresponding ends of the flossing material 90 may be received therein and securely wrapped around members 86. A cutting element 92 is provided on the flossing element I so that the flossing material may be cut to the desired size.

FIG. 7

Figure 7:
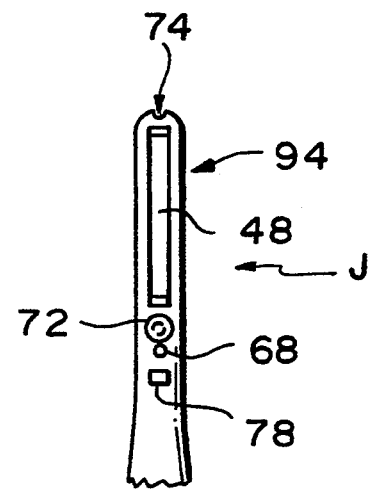
FIG. 7 is a fragmentary side elevational view of still a further alternative form of flossing implement.

Referring to FIG. 7, still a further alternative form is illustrated. This form combines the wrapped around floss feature illustrated in FIGS. 4 and 5 and the removable cartridge feature illustrated in FIGS. 2 and 3. Therefore, the individual has the option to either wrap the floss around the second end 94 of flossing element J exactly as shown in FIGS. 4 and 5 or use a removable cartridge illustrated in FIGS. 2 and 3. It should be noted that common elements have been numbered the same.

While this invention has been described as having a preferred design, it is understood that it is capable of further modifications, uses and/or adaption of the invention following in general the principle of the invention including such departures from the present disclosure as come within the known or customary practice in the art to which the invention pertains, and as may be applied to the central features set forth herein and fall within the scope of the invention and the limits of the appended claims.

I claim:

1. An apparatus for removing debris from between and around teeth, comprising:
   a) a main body member;
   b) a flossing implement connected to said main body member, said flossing implement having an exterior surface and an opening formed therein;
   c) said flossing implement including a pair of tines, said opening being disposed between said pair of tines;
   d) a removable floss support member being positioned in said flossing implement, said opening in said exterior surface being of sufficient size to permit said removable floss support member to be inserted in and removed from said flossing implement; and,
   e) said removable floss support member including a piece of floss material.
2. An apparatus as in claim 1, wherein:
   a) said flossing implement is detachably connected to said main body member.
3. An apparatus as in claim 1, further including:
   a) a drive motor drivingly connected to said flossing implement for reciprocally displacing said flossing element and the floss material.
4. An apparatus as in claim 3, wherein:
   a) said drive motor is positioned in said main body member.
5. An apparatus as in claim 3, further including:
   a) a protective cover for housing said flossing implement, said protective cover being positioned relative to said flossing implement such that upon actuation of said drive motor said flossing implement moves relative to said protective cover.
6. An apparatus as in claim 1, wherein:
   a) said flossing implement includes first and second ends, said first end of said flossing implement is positioned adjacent said main body member and said second end of said flossing implement is removed from said main body member, said second end of said flossing implement includes said pair of tines; and,
   b) said removable floss support member includes a pair of legs and an intermediate section connecting said pair of legs, said tines are hollow and of sufficient size to receive a corresponding leg of said removable floss support member.

7. An apparatus as in claim 1, wherein:
a) one of said flossing implement and said removable floss support member includes a stop for limiting movement of the floss material relative to an individual's teeth.

8. An apparatus as in claim 1, wherein:
a) said flossing implement includes a longitudinal axis, the floss material extends along the longitudinal axis of said flossing implement.

9. An apparatus as in claim 1, further including:
a) a drive motor drivingly connected to said flossing implement for displacing said flossing implement generally in a direction of extension of the floss material.

10. An apparatus for removing debris from between and around teeth, comprising:
a) a main body having first and second ends;
b) a flossing implement having first and second ends, said first end of said flossing implement being disposed adjacent said first end of said main body member, said second end of said flossing implement being removed from said first end of said main body member;
c) said second end of said flossing implement having first and second tines, said first tine being positioned closer to said first end of said main body member than said second tine;
d) a floss material extending in a first direction between said first and second tines;
e) a protective cover for housing said flossing implement wherein said protective cover remains secured around said flossing implement during use of said floss material; and
f) a drive motor operably associated with said flossing implement for displacing said flossing implement generally in the first direction.

11. An apparatus as in claim 10, wherein:
a) said protective cover is detachably connected to said main body member; and,
b) said flossing implement is detachably connected to said drive motor.

12. An apparatus as in claim 10, wherein:
a) said first and second tines each have an outwardly projecting member, said outwardly projecting members each having a recess for receiving the floss material.

13. An apparatus as in claim 10, wherein:
a) said flossing implement includes an exterior surface having an opening therein; and,
b) a removable floss support member positioned in said flossing implement, said opening in said exterior surface is of sufficient size to permit insertion and removal of said removable floss support member.

14. An apparatus as in claim 10, wherein:
a) said first and second tines each having a recess for receiving a portion of the floss material.

15. An apparatus as in claim 10, wherein:
a) said flossing implement includes a cutting element to cut a desired size of flossing material.

16. An apparatus for removing debris from between and around teeth, comprising:

a) a main body member having first and second ends;
b) a flossing implement having first and second ends, said first end of said flossing implement being disposed adjacent said first end of said main body member, said second end of said flossing implement being removed from said first end of said main body member;
c) said second end of said flossing implement including first and second tines, said first tine of said flossing implement being positioned closer to said first end of said main body member than said second tine, said first and second tines being adapted to support flossing material therebetween;
d) a protective cover for housing said flossing implement wherein said protective cover remains secured around said flossing implement during use of said floss material; and,
e) a drive motor operably associated with said flossing member for displacing said flossing member relative to said protective cover.

17. An apparatus as in claim 16, wherein:
a) said first and second tines each having a recess for receiving a portion of the floss material;
b) said flossing implement includes an outwardly projecting member adapted to receive both ends of the floss material; and,
c) said flossing implement further includes a cutting element for cutting the floss material to the desired size.

18. An apparatus as in claim 17, wherein:
a) said flossing implement includes an exterior surface and an opening formed therein; and,
b) a removable floss support member positioned in said flossing implement, said opening in said exterior surface is of sufficient size to permit insertion and removal of said removable floss support member.

19. An apparatus for removing debris from between and around teeth, comprising:
a) a main body member;
b) a flossing implement connected to said main body member, said flossing implement having an exterior surface and an opening formed therein;
c) a removable floss support member being positioned in said flossing implement, said opening in said exterior surface being of sufficient size to permit said removable floss support member to be inserted in and removed from said flossing implement;
d) said removable floss support member including a piece of floss material;
e) said flossing implement including first and second ends, said first end of said flossing implement being positioned adjacent said main body member and said second end of said flossing implement being removed from said main body member, said second end of said flossing implement including a pair of tines; and,
f) said removable floss support member including a pair of legs and an intermediate section connecting said pair of legs, said tines being adapted to receive a corresponding leg of said removable floss support member.

* * * * *